United States Patent [19]
Gelman

[11] Patent Number: 5,910,442
[45] Date of Patent: *Jun. 8, 1999

[54] TUMOR SUPPRESSOR GENE

[75] Inventor: Irwin H. Gelman, New York, N.Y.

[73] Assignee: Mount Sinai School Of Medicine, NY, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/635,121

[22] Filed: Apr. 19, 1996

[51] Int. Cl.$^6$ .......................... C12N 15/11; C12N 15/09; C12N 5/10; C12N 15/79

[52] U.S. Cl. .................. 435/325; 435/252.3; 435/172.3; 435/320.1; 536/23.1; 536/23.5

[58] Field of Search ........................ 536/23.1; 435/320.1, 435/325, 375, 172.3, 69.1, 7.9, 252.3; 514/44

[56] References Cited

PUBLICATIONS

Marshall, E (1995) Science 269: 1050–1055.
Miller et al (1995) FASEB J. 9: 190–199.
Sager, 1989, Science 246:1406–1412.
Lee et al., 1991, Proc. Natl. Acad. Sci. USA 88:2825–2829.
Gluck, 1993, Proc. Natl. Acad. Sci. USA, 90:383–387.
Hirada et al., 1993, Science, 259: 971–974.
Levine et al., 1993, Ann. Rev. Biochem. 62:623–651.
Prasda et al., 1993, Proc. Natl. Acad. Sci. USA 90:7039–7043.
Contente et al., 1993, Science 249:796–798.
Houle et al., 1993, Proc. Natl. Acad. Sci. USA 90:985–989.
Mishra et al., 1994, J. Cell. Biochem. 18 (Supp):171.
Ozaki et al., 1994, Cancer Res. 54:646–648.
Zou et al., 1994, Science 263: 526–529.
Lin et al., 1995, Mol. Cell. Biol. 15:2754–2762.
Gelman et al., 1995, Genebank Accession No. RNU23146.
Gelman et al., 1996, Genebank Accession No. A57376.
Lin et al., 1996, J. Biol. Chemistry 45:28430–28438.

*Primary Examiner*—Brian R. Stanton
*Assistant Examiner*—Karen M. Hauda

[57] ABSTRACT

The present invention relates to a novel tumor suppressor gene, SSeCKSS. It is based, at least in part, on the discovery of a gene, hitherto referred to as "322" (Lin et al., 1995, Mol. Cell. Biol. 15:2754–2762) but now referred to as SSeCKS, which was found to be down-regulated in certain transformed cells. Further, the SSeCKS gene product was subsequently shown to be a substrate of protein kinase C. SSeCKS protein has been shown to act as a mitogenic regulator and as an inhibitor of the transformed phenotype.

3 Claims, 18 Drawing Sheets

```
  1 ggaaaagacagagccagcctcggaggagcaggagccggcagaagacacagaccaggccag                  60
 61 gttgtcagcagactacgagaaggtggagctgcctttggaagaaccaggttggtgacctga                 120
121 ggcatcgtcagaggagaagtgtgctccttggcaacggaagtgtttgatgagaagatgga                 180
                                                              M  E              2

181 agccccaccagaagttgttgcagaggtccacgtgagccgtggagaacagaggagga                     240
     A  H  Q  E  V  V  A  E  V  E  V  S  T  V  E  K  T  E  E  E                22

241 gcagggaggagaggctgaaggggggaggctgtggtggtagaaggaacaggagaatcctt                  300
     Q  G  G  G  E  A  E  G  G  V  V  V  E  G  T  G  E  S  L                   42

301 gcccctgaaactggctgagcctgagcccccaggaggtccccaggaagctgagcctgctgagga             360
     P  P  E  K  L  A  E  P  Q  E  V  P  Q  E  A  E  P  A  E  E                62

361 gctgatgaagagcagagagatgtgtctctggaggagaccacactgacagacct                        420
     L  M  K  S  R  E  M  C  V  E  G  G  D  H  T  Q  L  T  D  L                82

421 aagtcctgagagagaagacgctgccaaactgaaggcattgtcagtgaggtggagat                     480
     S  P  E  E  K  T  L  P  K  H  P  E  G  I  V  S  E  V  E  M               102

481 gctgtcctctcaggaaagaatcaaggtacagggaagtccctgaagaactcttcagtag                   540
     L  S  S  Q  E  R  I  K  V  Q  G  S  P  L  K  K  L  F  S  S               122

541 ctcaggcttaaagaagctgtctgggaagaagcagaagggaaacgaggaggtggggaga                   600
     S  G  L  K  K  L  S  G  K  K  Q  K  G  K  R  G  G  G  D                  142

601 cgaagagcctggagaataccaacacattcacaccgaatcccagagagtgctgatgagca                  660
     E  E  P  G  E  Y  Q  H  I  H  T  E  S  P  E  S  A  D  E  Q               162
```

FIG.3A

| | | |
|---|---|---|
| 661 | gaagggagagctctgcgtcgtccccgaggagcctgaggagaccacgtgtctggagaa | 720 |
| 163 | K G E S S A S S P E E P E E T T C L E K | 182 |
| 721 | agggccgctgaagcaccccaggatgggaagctgaggaagaactacttcgtggagaa | 780 |
| 183 | G P L E A P R M G K L R K E L L R G E K | 202 |
| 781 | gaagaggaaggatcactccctggcatccttcaaaagatgtgacaccaagaaacggt | 840 |
| 203 | K R K D H S L G I L Q K D G D T Q E T V | 222 |
| 841 | ccgaagaccttctgagagtgacaaggaggaagagctggagaaggtcaagagcgccacctt | 900 |
| 223 | R R P S E S D K E E L E K V K S A T L | 242 |
| 901 | gtcctccactgatagcacagtgtcagaaatgcaagatgaagtcaaaactgttggtgagga | 960 |
| 243 | S S T D S T V S E M Q D E V K T V G E E | 262 |
| 961 | acaaaagccagagaccaaagcgtaggtggatacttcagtgtcttgggaagcactgat | 1020 |
| 263 | Q K P E E P K R R V D T S V S W E A L I | 282 |
| 1021 | ttgtgtcggatcatccaagaagacaaggaagcatctcttcagatataagagggcc | 1080 |
| 283 | C V G S S K K R A R K A S S S D I R G P | 302 |
| 1081 | aaggacactgggagggggacagtcacagagcagagagggccagcaaagacaaagaagccg | 1140 |
| 303 | R T L G G Q S R G G Q Q R Q R S R | 322 |
| 1141 | aacagacgctgttcctgccagcaccagaggaccaagcgcaaggaagttcctcacc | 1200 |
| 323 | T D A V P A S T Q E Q D Q A Q G S S S P | 342 |
| 1201 | cgagccagcggaagccctttcgaaggggaaggtgtctccacttgggagtcatttaaaag | 1260 |
| 343 | E P A G S P S E G E G V S T W E S F K R | 362 |

FIG. 3B

```
1261  attgtcactccaagaaaaaatccaagtcaaactggaagagaagagccggaaggac  1320
363   L  V  T  P  R  K  K  S  K  S  K  L  E  E  K  E  A  G  R  T   382

1321  tctagttgtaggagacaggttgtccactgagatcgaaccgtgtagagaagaatcttgggtt  1380
383   L  V  V  G  A  G  C  P  L  R  S  N  R  V  E  K  N  L  G  F   402

1381  tccattaagaaattcatcccgacggcggaagaaaagggcagatgggaaggcaagaaca     1440
403   P  L  R  N  S  S  P  D  G  G  R  K  G  Q  M  G  R  Q  E  Q   422

1441  agccactgtggaagactcagggccagtggagataaatgaggacgagcctgatgtcccagc  1500
423   A  T  V  E  D  S  G  P  V  E  I  N  E  D  E  P  D  V  P  A   442

1501  agtcgtgcctctgtctgagtatgatcagtggaggagaagaagatggaagccagggaa     1560
443   V  V  P  L  S  E  Y  D  A  V  E  R  E  K  M  E  A  Q  G  N   462

1561  tgcggagctgccagctgcgggtgcgtgtgtagtgtccgagagctcagtaagactctggt  1620
463   A  E  L  P  S  C  W  G  C  V  V  S  E  E  L  S  K  T  L  V   482

1621  ccacactgtgagtcgcagtcgcattgatgggaccagggcagtgtcaccagtgtcgaagagcg  1680
483   H  T  V  S  V  A  V  I  D  G  T  R  A  K  T  S  K  E  E  R   502

1681  gtctccttcgtggatatccgcttccgttaacagaacctcttgaacacacagcggagaagc  1740
503   S  P  S  W  I  S  A  S  V  T  E  P  L  E  H  T  A  G  E  A   522

1741  catgccacctgttgaagaggtcactgaaaagacatcattgcagaagaaactcctgtgct  1800
523   M  P  P  V  E  E  V  T  E  K  D  I  I  A  E  E  T  P  V  L   542

1801  cacccagacgttaccagagggtaaagatgccatgacgacatggtcaccagtgaagtgga  1860
543   T  Q  T  L  P  E  G  K  D  A  H  D  D  M  V  T  S  E  V  D   562
```

FIG.3C

| | | |
|---|---|---|
| 1861 | tttcacctcagaagctgtgacagccacagagacctcagaggctcctcgtactgaagaagt | 1920 |
| 563 | F  T  S  E  A  V  T  A  T  E  T  S  E  A  L  R  T  E  E  V | 582 |
| 1921 | taccgaagcatcgggggccgagagaccacagacatggtgtccgcagtttcccagctgac | 1980 |
| 583 | T  E  A  S  G  A  E  E  T  T  D  M  V  S  A  V  S  Q  L  T | 602 |
| 1981 | tgactccccagacaccagaggagccaccccagttcaggaggtagagggtgtgtgct | 2040 |
| 603 | D  S  P  D  T  T  E  E  A  T  P  V  Q  E  V  E  G  G  V  L | 622 |
| 2041 | agatacagaagagaggagcgccagacgcaggccatcctccaagccgttgcagacaaggt | 2100 |
| 623 | D  T  E  E  E  R  Q  T  Q  A  I  L  Q  A  V  A  D  K  V | 642 |
| 2101 | gaaagaggagtccaggtgcctgcaacccagactgtgcagagaacggggtcaaaagcact | 2160 |
| 643 | K  E  E  S  Q  V  P  A  T  Q  T  V  Q  R  T  G  S  K  A  L | 662 |
| 2161 | gggaaggtttgaggagtagaggaggactccgaagtgctggcttcggagaaagagaagga | 2220 |
| 663 | E  K  V  E  E  V  E  E  D  S  E  V  L  A  S  E  K  E  K  D | 682 |
| 2221 | cgttatgccgaaaggaccccgtgcaggaagctgagctgagcatcttgcacagggctctga | 2280 |
| 683 | V  M  P  K  G  P  V  Q  E  A  E  H  L  A  Q  G  S  E | 702 |
| 2281 | gactggacaggctactccagagagccttgaagttcctgaagtcacagcagatgtagacca | 2340 |
| 703 | T  G  Q  A  T  P  E  S  L  E  V  P  E  V  T  A  D  V  D  H | 722 |
| 2341 | tgtgccacgtgccagttatcaagctccagcagctgatggaacaggccgtggccctga | 2400 |
| 723 | V  A  T  C  Q  V  I  K  L  Q  Q  L  M  E  Q  A  V  A  P  E | 742 |
| 2401 | gtcatccgaaacctgacagacagtgagacaaatgaagcactccctagcagattcaga | 2460 |
| 743 | S  S  E  T  L  T  D  S  E  T  N  G  S  T  R  L  A  D  S  D | 762 |

FIG.3D

| | | |
|---|---|---|
| 2461 | cactgcagatggggacacagcaagatgaaccattgacagcagcaggacagtaaagccactgc | 2520 |
| 763 | T A D G T Q Q D E T I D S Q D S K A T A | 782 |
| 2521 | agctgtcaggcagtcacagtcacagagaagaggcggctactgctcagaaagaggagcc | 2580 |
| 783 | A V E Q S Q V T E E A A T A Q K E E P | 802 |
| 2581 | ttcgacactacctaataatgttccagccaggaagacatgggaagaaccaggaagaga | 2640 |
| 803 | S T L P N N V P A Q E E H G E E P G R D | 822 |
| 2641 | tgttcttgaacctacacagcaagacttgctgctgcagccgtgcccgtctggcaaaagac | 2700 |
| 823 | V L E P T Q Q E L A A A A V P V W Q K T | 842 |
| 2701 | tgaggtgggtcaagaggggtgaggttgactgttggatggaaaaagtcaaagaagaaca | 2760 |
| 843 | E V G Q E G E V D W L D G E K V K E E Q | 862 |
| 2761 | ggaggtgttttgtacactctgaccaacagtcaaaaggctgctgatgtgacatatgacag | 2820 |
| 863 | E V F V H S G P N S Q K A A D V T Y D S | 882 |
| 2821 | tgaagtgatgggagtggccggggtgtcaggaaaaggagagtactgaagtgcagagtcttag | 2880 |
| 883 | E V M G V A G C Q E K E S T E V Q S L S | 902 |
| 2882 | cctggagaggagagatggaaactgacgttgaaaagagagaaaaggagacaaagccaga | 2940 |
| 903 | L E E G E M E T D V E K E K R E T K P E | 922 |
| 2941 | gcaagtgagtgaagaaggtgagcaggaaacagccgctcctgagcatgaaaggaactacgg | 3000 |
| 923 | Q V S E E G E Q E T A A P E H E R N Y G | 942 |
| 3001 | gaagccagtcctgacactgacatgcccagtcagagagggaaggcactgggaagcct | 3060 |
| 943 | K P V L T L D M P S S E R G K A L G S L | 962 |

FIG.3E

| | | |
|---|---|---|
| 3061 | tggaggaagcccttctctcccagaccaagacaaagcaggttgcatagaggttcaagttca | 3120 |
| 963 | G G S P S L P D D Q D K A G C I E V Q V Q | 982 |
| 3121 | aagcctgacacacagtcactcaaacagcagaagctgtggaaaaggtcatagaaacggt | 3180 |
| 983 | S L D T T V T Q T A E A V E K V I E T V | 1002 |
| 3181 | tgtgatttcagagacaggtgaaagtccagagtgtgtaggtgcacacttattaccagctga | 3240 |
| 1003 | V I S E T G E S P E C V G A H L L P A E | 1002 |
| | →Zn-finger→ | |
| 3241 | gaagtcctctgcaacgggtggccactggacttcttcagcatgcagaggacacggtacccct | 3300 |
| 1023 | K S S A T G G H W T L Q H A E D T V P L | 1042 |
| 3301 | ggggcctgagtcctcaggcagaatccatccaatcatagtaactcctgctcctgaaagcac | 3360 |
| 1043 | G P E S Q A E S I P I I V T P A P E S T | 1062 |
| 3361 | cctacatcctgacctacaaggagagagcatcccagagagagcgatcagaggaaga | 3420 |
| 1063 | L H P D L Q G E I S A S Q R E R S E E E | 1082 |
| 3421 | ggacaagccagatgctggtcctgatgctgacggcaaggagagtacagcaatcgacaaagt | 3480 |
| 1083 | D K P D D A G P D A D G K E S T A I D K V | 1102 |
| 3481 | cctcaaggctgaacctgagatcctgagaacttgagagtaagagcaacaagattgtgctgaa | 3540 |
| 1103 | L K A E P E I L E L E S K S N K I V L N | 1122 |
| 3541 | cgtcattcagacagccgttgaccagttcgcacgtacagaaacagccccgaaactcatgc | 3600 |
| 1123 | V I Q T A V D Q F A R T E T A P E T H A | 1142 |
| 3601 | ttatgattcacagacccaggttcctgcaatgcgcttggacagcaggagcccaacagatg | 3660 |
| 1143 | Y D S Q T Q V P A M R L D S R E P N R C | 1162 |

FIG.3F

| | | | |
|---|---|---|---|
| 3661 | ctggacaaaatgaagttgccaagatgaaacaccagtgccgcagccagagagactt | 3720 | |
| 1163 | W T K M K V A K M K H P V P Q P R E D L | 1182 | |
| 3721 | gcaagtcctgaccgttctggaggcatggctcagctcggaaatgcttgccgccttgcagt | 3780 | |
| 1183 | Q V L T V L E A W L S S E M L A A L A V | 1202 | |
| 3781 | tgaaagcgccggtgtcaaagtaagcattgagaagctgcctcctcaaccaaagatcaaaa | 3840 | |
| 1203 | E S A G V K V S I E K L P P Q P K D Q K | 1222 | |
| 3841 | ggagcatgctgctgatgccctcagctccaaagcttagccaggcagaggcagtgtctgg | 3900 | |
| 1223 | E H A A D G P Q L Q S L A Q A E A V S G | 1242 | |
| 3901 | aaacctaaccaaagaatcccagaccaaccgaccaaagctaaccgaggagcgatgccc | 3960 | |
| 1243 | N L T K E S P D T N G P K L T E E R C P | 1262 | |
| 3961 | ccaaaagttgaggtccaggaagaagaaaatgtctaccaagtcagtcagtcaaagaacaaggcc | 4020 | |
| 1263 | Q K L R S R K K K C L P S Q S K R T R P | 1282 | |
| 4021 | caggcagagagacctgcaggagccaaaggagacctggcagaatcctaagatgttagt | 4080 | |
| 1283 | R Q K R T C R S Q R E T W Q N P K M L V | 1302 | |
| 4081 | tgctcattgtacatctgtaagaccagaatgtgaaaacaagtcacagaacaagatgctgct | 4140 | |
| 1303 | A H C T S V R P E C E N K S Q N K M L L | 1322 | |
| 4141 | gttgggacctttggaccaagatttcagagccccatgagagagcagggccgtccaat | 4200 | |
| 1323 | L G P W T K I S E P M R S R E Q G R P M | 1342 | |
| 4201 | gatttccaccagtagagcaccccgacaattctgaggcttcatcggggagctagagccagc | 4260 | |
| 1343 | I S T Q * | 1346 | |

FIG. 3G

| | | |
|---|---|---|
| 4261 | taacatttcctcgtttcaagactgctttgatttgcccctttgatgccgtccgtgtatttc | 4320 |
| 4321 | ggatttaaggtcctgcgttcctcaacctggaaccaattctgccatacctagttccacttct | 4380 |
| 4381 | caaactggagcatcctccttatgtatttatatgtttatgtttctcctcctgt | 4440 |
| 4441 | acctattgtatattttttctaacgttaagcacatgctttttgtattatgcaatatata | 4500 |
| 4501 | acgggtgtgcagccatagcgacgctttgaaaagctccagcctcaactgtaacctgcagc | 4560 |
| 4561 | aaacagataacattcctgcaagaagagacaagtcttttttaagtttactgatgcttag | 4620 |
| 4621 | atctgtgggctttctagtcctctgaaagtggttgttttcctatgcacagcgagctcagaaa | 4680 |
| 4681 | taaaaccccattttgaaacatccaggatgtcccaatattaccatgatttttttcccct | 4720 |
| 4721 | ttttgctaatccagtccagttggaaagaagtctcctcgtgtcagattaagccctgtct | 4780 |
| 4781 | cttaatgatatggacaaatgagtgtgcctaaggccatgagatgtttcctaatgcagaagg | 4840 |
| 4841 | aatctgttgtacgttttttgattgtactcttctatgctggaccgaattcatatgcagat | 4900 |
| 4901 | cgaagtgagtcctgttctttacagatggtatttgatagatactggagttgtctgtgtt | 4960 |
| 4961 | atatctgtgccctttgttcttttaagaacaatgttgcattatgttccttttggataaattgtgat | 5020 |
| 5021 | ttgacaactgattaaataaacatatttgactac(A). | |

FIG.3H

TUMOR SUPPRESSOR GENE

SPECIFICATION

The invention contained herein is based, at least in part, on research funded by NIH grant number NIH CA65787. Accordingly, the United States government may have certain rights herein.

INTRODUCTION

The present invention relates to a novel tumor suppressor gene, referred to herein as SSeCKS, its encoded protein, and methods of use thereof. It is based, at least in part, on the discovery of a SSeCKS gene which encodes a substrate of protein kinase C that functions as both a mitogenic regulator as well as a tumor suppressor.

BACKGROUND OF THE INVENTION

The inactivation of several tumor suppressor gene families (for example, those encoding p53, Rb, and APC) as a result of mutation is acknowledged to contribute to oncogenicity of several types of human cancers (Levine, 1993, Ann. Rev. Biochem. 62:623–651). Many of these so-called class I tumor suppressor genes (Lee et al., 1991, Proc. Natl. Acad. Sci. U.S.A. 88:2825–2829) were identified and isolated following cumbersome pedigree and cytogenetic analyses (Sager, 1989, Science 246:1406–1412). Recently, another class of genes (class II) whose expression is known to be down-regulated in tumor cells has been shown by gene transfer techniques to encode potential tumor suppressors. These include nonmuscle α-actinin, tropomyosin I, CLP, retinoic acid receptor $\beta_1$, and interferon regulatory factor (Gluck et al., 1993, Proc. Natl. Acad Sci. U.S.A. 90:383–387; Hirada et al., 1993, Science 259:971–974; Hogel et al., 1993, Proc. Natl. Acad. Sci. U.S.A. 90:985–989; Mishra et al., 1994, J. Cell. Biochem. 18 (Supp. C):171; Plasad et al., 1993, Proc. Natl. Acad. Sci. U.S.A. 90:7039–7043). Additional tumor suppressor gene families such as the maspin gene, rrg, and NO3 (Contente et al., 1993, Science 249:796–798; Ozaki et al., 1994, Cancer Res. 54:646–648; Zou et al., 1994, Science 263:526–529) were isolated by subtractive hybridization techniques designed to identify down-regulated genes. The ability of these genes to reverse an array of oncogenic phenotypes following gene transfer and overexpression supports the possibility for novel therapeutic modalities for cancer.

SUMMARY OF THE INVENTION

The present invention relates to a novel tumor suppressor gene, SSeCKS. It is based, at least in part, on the discovery of a gene, hitherto referred to as "322" (Lin et al., 1995, Mol. Cell. Biol. 15:2754–2762) but now referred to as SSeCKS, which was found to be down-regulated in certain transformed cells. Further, the SSeCKS gene product was subsequently shown to be a substrate of protein kinase C. SSeCKS protein has been shown to act as a mitogenic regulator and as an inhibitor of the transformed phenotype.

In various embodiments, the present invention relates to the SSeCKS gene and protein, and in particular, to rat and human SSeCKS gene and protein. Furthermore, the present invention provides for the use of such genes and proteins in diagnostic and therapeutic methods.

BRIEF DESCRIPTION OF THE DRAWINGS

FIGS. 3A–H. Nucleic acid SEQ ID NO:1 (top line, lower case letters) and deduced amino SEQ ID NO:2 acid (lower line, capital letters) sequence of rat SSeCKS cDNA.

DETAILED DESCRIPTION OF THE INVENTION

Figure 1:
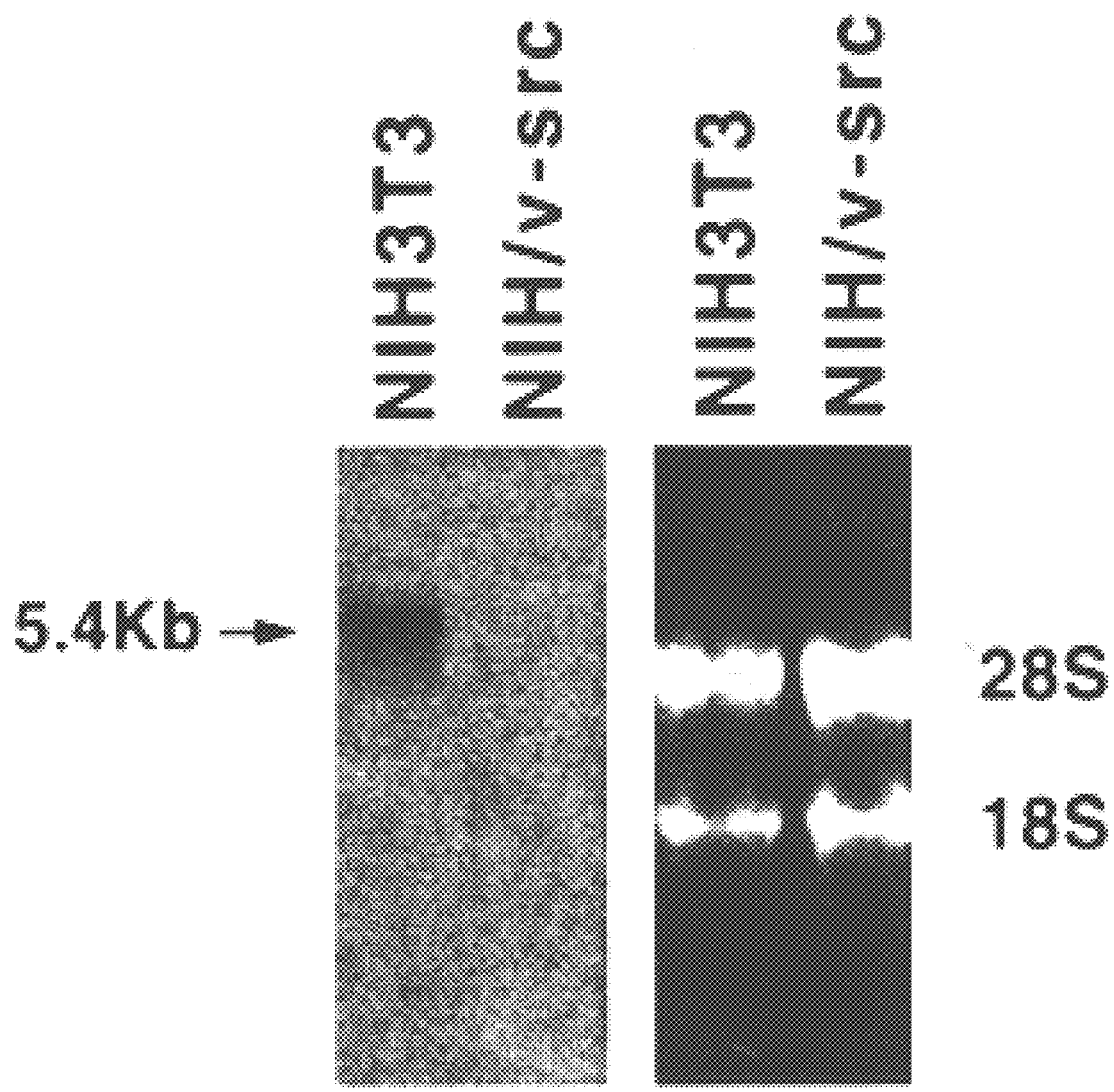
FIG. 1. Northern blot analysis of SSeCKS RNA levels in NIH 3T3 cells versus NIH/v-src transformed cells.

The present invention relates to SSeCKS genes and proteins.

In one specific embodiment, the present invention relates to a purified and isolated nucleic acid molecule having the nucleic acid sequence set forth in FIG. 3, which is the rat SSeCKS cDNA. In another embodiment, the present invention relates to a purified and isolated nucleic acid molecule which hybridizes to a nucleic acid molecule having a sequence as set forth in FIG. 3 SEQ ID NO:1 under stringent hybridization conditions. This embodiment would include nucleic acid molecules from species other than rat, such as the human SSeCKS cDNA. This embodiment would also relate to genomic DNA and RNA molecules. Stringent hybridization conditions are as described in Maniatis et al., 1982, in *Molecular Cloning: A Laboratory Manual,* Cold Spring Harbor Laboratory, Cold Spring Harbor, N.Y. In one specific, nonlimiting embodiment of the invention, stringent hybridization may be performed between DNA molecules in the Southern method, in a solution of 0.75M sodium phosphate pH 7, 1 mM EDTA, 7% SDS, 1% bovine serum albumin (BSA), and 100 microgram per ml salmon sperm DNA for 12–18 hours at 65 degrees centigrade, followed by washing twice in 50 mM sodium phosphate, 1 mM EDTA, 1% SDS, and 0.5% BSA at 65 degrees C., and twice again in the same solution without BSA at 65 degrees centigrade.

In a related embodiment, the present invention provides for a purified and isolated nucleic acid sequence which is at least 90 percent homologous to the nucleic acid molecule having a sequence as set forth in FIG. 3.

In further embodiments, the present invention provides for a purified and isolated protein having an amino acid sequence as set forth in FIG. 3 SEQ ID NO:1. The present invention also provides for a purified and isolated protein encoded by a nucleic acid molecule having the sequence set forth in FIG. 3 or (i) a nucleic acid molecule which hybridizes thereto under stringent conditions or (ii) is at least 90 percent homologous thereto.

The present invention also relates to vectors comprising the abovementioned nucleic acid molecules, including plasmid, phage, cosmid, and viral vectors. The foregoing nucleic acid molecules may be combined, in such vectors or otherwise, with nucleic acid sequences which may aid in their expression, including promoter/enhancer sequences and other sequences which aid in transcription, translation, or processing. Vectors of the invention may further comprise other sequences, such as selection markers, as used by skilled artisans.

The present invention further provides for antibodies, including monoclonal or polyclonal antibodies, directed toward the proteins of the invention, and prepared by standard techniques known in the art. It may be desirable to subject such antibodies to purification using an affinity column to which SSeCK protein is bound.

The molecules of the present invention have a number of utilities. As described in the example section below, suppression of SSeCKS expression occurs in association with transformation by certain oncogenes or by the triggering of a proliferative cycle in starved cells by the addition of serum to the growth medium. These observations indicate that SSeCKS acts as a negative regulator of mitosis. As such, the introduction of SSeCKS gene or protein into a host cell may be used to inhibit mitosis of the host cell. Introduction may be achieved either via a vector, by physical means, or by direct uptake of the SSeCKS gene or protein into the host cell.

Moreover, it has been discovered that ectopic expression of SSeCKS suppressed the ability of v-src to induce morphological transformation and anchorage-independent growth in rodent fibroblasts. Thus, the introduction of SSeCKS gene or protein into a cell may be used to inhibit the expression of a transformed phenotype by the cell.

Since many human diseases are associated with disorders of proliferation and/or with the expression of a malignant (i.e. transformed) phenotype, increasing the levels of SSeCKS DNA, mRNA, and/or protein in a patient suffering from such a disease may be beneficial. For example, the levels of SSeCKS may be increased in a malignant tumor in such a patient in order to decrease its propensity to metastasize.

Furthermore, the level of SSeCKS expression in a cell or collection of cells may be used to evaluate the mitotic state of such cells, where a low level of SSeCKS expression may bear a positive correlation with active mitosis. Furthermore, a low level of SSeCKS expression may bear a positive correlation with a malignant phenotype. Such measurements may be used in the diagnosis or staging of malignancy, or in the assessment of the effects of therapeutic interventions in a subject in need of such treatment.

EXAMPLE: CLONING AND CHARACTERIZATION OF SSeCKS cDNAs were identified whose abundance is low in NIH 3T3 cells and decreased following the expression of the activated oncogene v-src. The transcription of one such gene, SSeCKS (pronounced "ESSEX"), was found to be suppressed at least 15-fold in src, ras, and fos-transformed cells and 3-fold in myc-transformed cells, but was unaffected in raf, mos, or neu-transformed cells. Activation of a ts-v-src temperature sensitive allele in confluent 3Y1 fibroblasts resulted in an initial increase in SSeCKS mRNA levels after 1 to 2 hours followed by a rapid decrease to suppressed levels after 4 to 8 hours. Morphological transformation was not detected until 12 hours later, indicating that the accumulation of SSeCKS transcripts is regulated by v-src and not as a consequence of transformation. Addition of fetal calf serum to starved subconfluent NIH 3T3 or 3Y1 fibroblasts resulted in a similar biphasic regulation of SSeCKS, indicating that SSeCKS transcription is responsive to mitogenic factors. Sequence analysis of a full-length SSeCKS cDNA rat clone (5.4 kb) identified a large open reading frame encoding a 148.1 kDa product, but in vitro transcription-translation from a T7 promoter resulted in a 207 kDa product. Further, sequence analysis indicated that SSeCKS has only limited homology to known genes, including the human gravin gene, where a small amount of homology exists in the 3' untranslated region. Particular data relating to these conclusions is set forth in greater detail below.

FIG. 1 depicts the results of Northern blot analysis of SSeCKS RNA levels in NIH 3T3 cells versus NIH/v-src transformed cells. A 30 microgram amount of total RNA purified by the RNAzol method from NIH 3T3 cells or NIH/v-src cells was electrophoresed through a 1% agarose-1formaldehyde gel, blotted onto Immulon N membrane, hybridized with a $_{32}$P-labelled CDNA insert containing SSeCKS sequence, washed, and autoradiographed for 3 weeks. The amount of RNA loaded was normalized by densitometric analysis of 28S and 18S RNA bands (right panel).

Figure 2A:
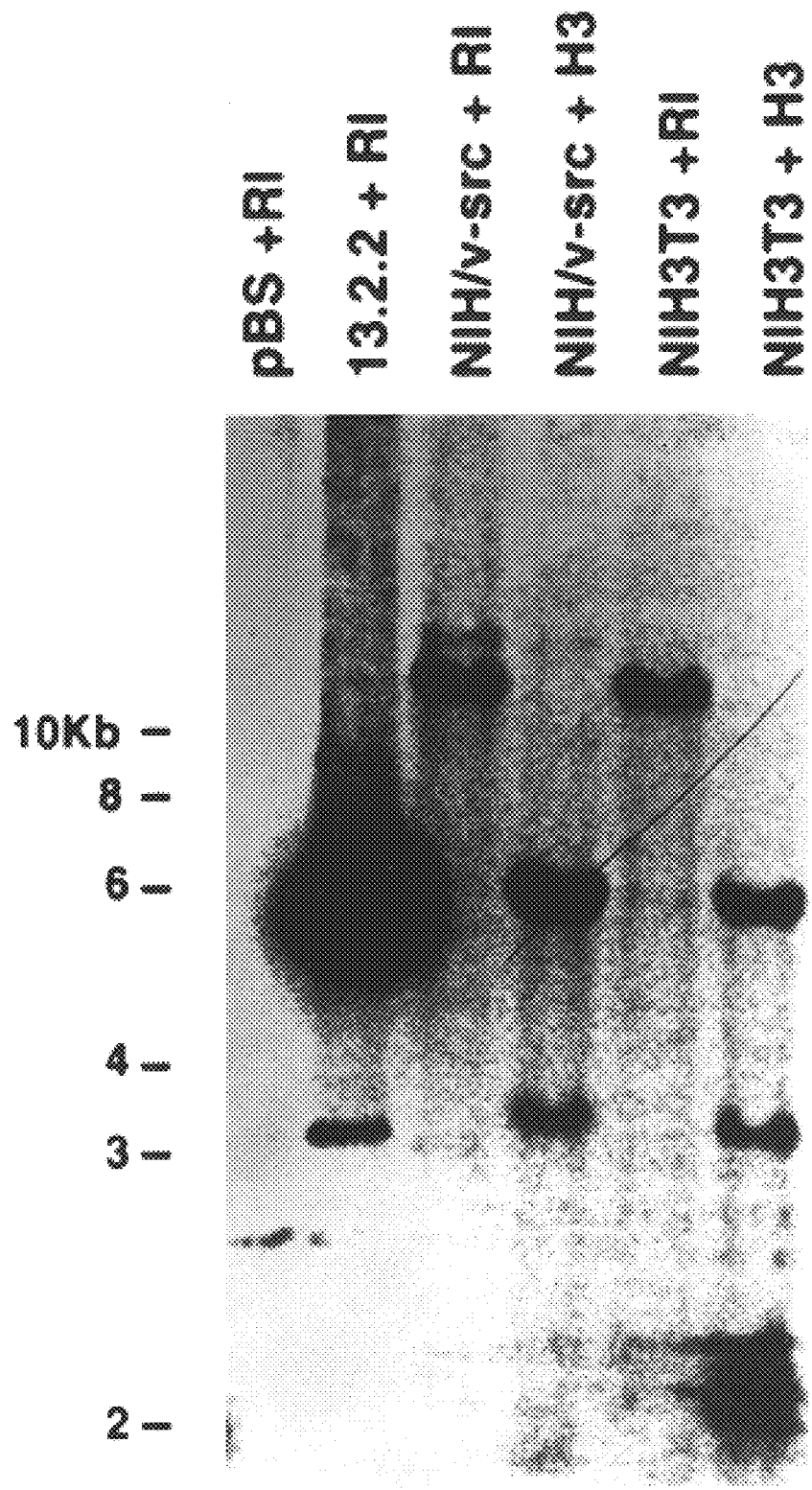
FIG. 2A & B. Southern blot analysis showing that the decreased level of SSeCKS RNA in NIH/v-src cells is not due to gross deletion or translocation of the SSeCKS allele, and restriction map of SSeCKS.
Figure 2B:
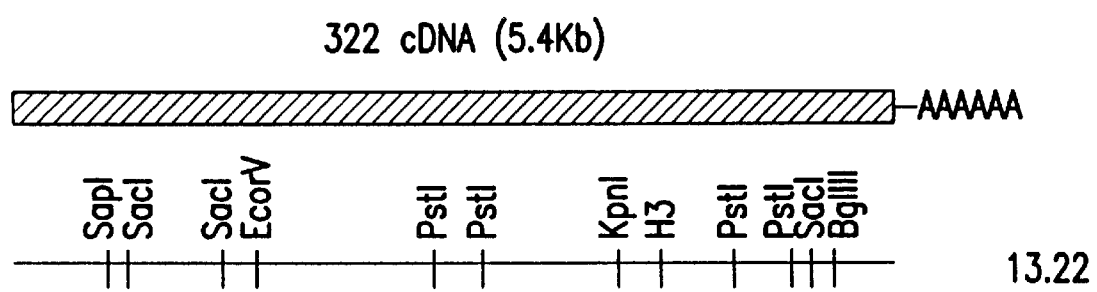

FIG. 2 shows that the decreased level of SSeCKS RNA in NIH/v-src cells is not due to gross deletion or translocation of the SSeCKS allele. As shown in the top panel, a 20 microgram amount of genomic DNA from NIH 3T3 or NIV v-src cells was digested to completion with EcoRI or HindIII, electrophoresed through a 0.7% agarose gel, and then blotted onto Immobilon N membrane. Fifty picogram amounts of EcoRI-cut pBluescript II KS and SSeCKS plasmid DNA were included as negative and positive controls, respectively. The blot was hybridized as described in the legend to FIG. 1, and autoradiographed for 2 days with an intensifying screen. DNA molecular size standards are shown on the left. RI refers to EcoRI, H3 refers to HindIII. The bottom panel shows the restriction map of full length SSeCKS RNA, and clone 13.2.2, isolated from a rat 3T3 library. Much of this restriction pattern is shared by both mouse and rat SSeCKS homologs, although only the rat allele contains an internal EcoRI site approximately 250 bp from the 3' cDNA terminus.

FIG. 3 depicts the nucleic acid SEQ ID NO:1 (top line, lower case letters) and deduced amino acid SEQ ID NO:2 (lower line, capital letters) sequence of rat SSeCKS cDNA. The largest open reading frame (from bases 176 to 4213) was identified using the TRANSLATE program from Genetics Computer Group (by J, Devereux, 1993, in Madison, Wis.). Glycine-rich domains in the N-terminus are underlined. Nuclear localization signals fitting th motif K(R/K)X (R/K) are boxed. A sequence consistent with a Zn finger from bases 3211 to 3280 is in boldface type. Two polyadenylation signals (AATAAA) in the 3' untranslated region are underlined.

Figure 4A:
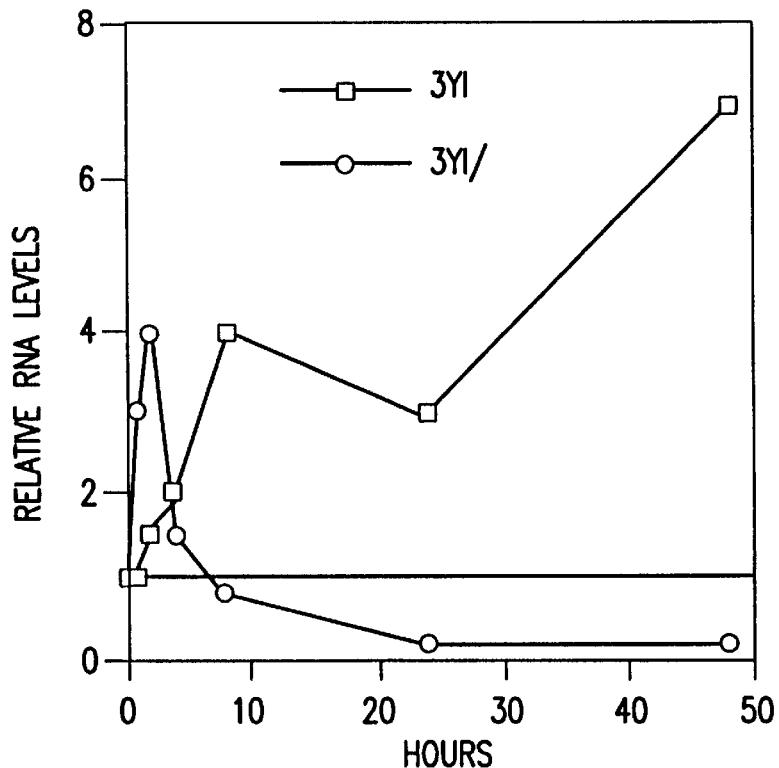
FIG. 4A & B. Northern blot analysis showing that the transcription of SSeCKS is suppressed relatively soon after the activation of a ts-src allele (A) or the addition of fetal calf serum (FCS) to starved rodent fibroblasts (B).
Figure 4B:
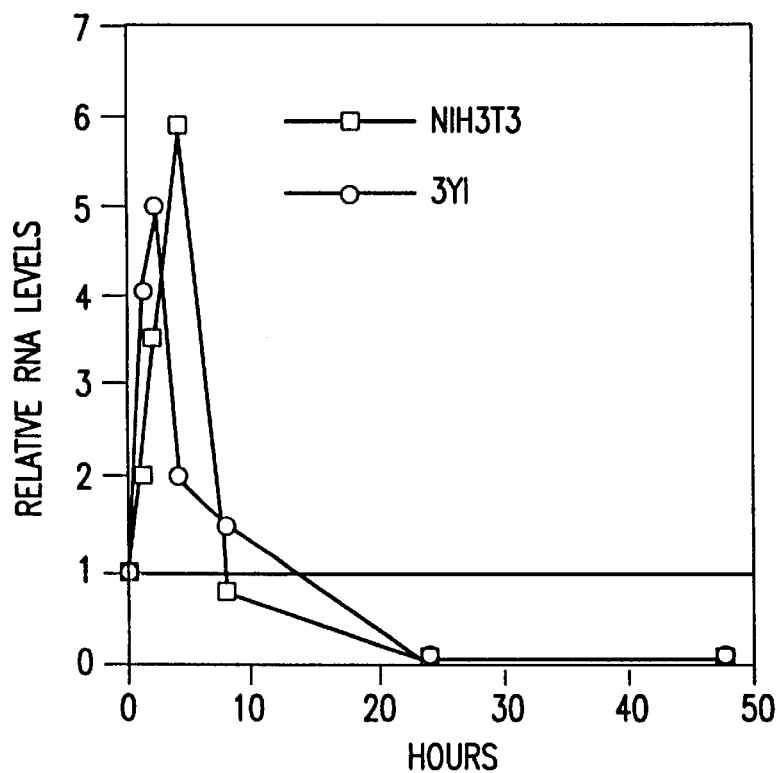

FIG. 4 shows that the transcription of SSeCKS was suppressed relatively soon after the activation of a ts-src allele or the addition of fetal calf serum (FCS) to starved rodent fibroblasts. FIG. 4A depicts the results of experiments wherein 3Y1/ts72src cells or parental rat 3Y1 fibroblasts were grown at the nonpermissive temperature (NPT; 39.5 degrees C) for 24 hours and then shifted to the permissive temperature (PT) for v-src activity (35 degrees C). Morphological transformation was not apparent until roughly 24 hours after the temperature downshift. The level of SSeCKS RNA dropped precipitously in the transformed cells but not their untransformed counterparts. FIG. 4B shows the results of experiments in which NIH 3T3 cells and 3Y1 cells were incubated overnight with 0.25% FCS and then with 10% FCS. Total RNA isolated at various times from each cell line was analyzed for SSeCKS transcription by Northern blot analysis using $^{32}$P-labelled SSeCKS probe. Soon after the addition of 10% FCS, the levels of SSeCKS decreased rapidly in both cell lines. The cells used for panel A were seeded at confluency at the start of the experiment whereas the cells used for panel B were subconfluent throughout the experiment.

Figure 5:
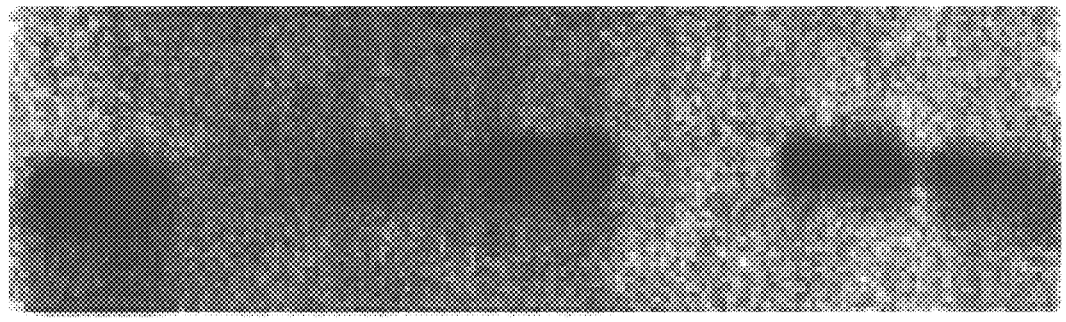
FIG. 5. Northern blot analyses showing levels of SSeCKS transcripts in oncogene-transformed Rat-6 fibroblasts.

FIG. 5 shows the results of Northern blot analyses showing levels of SSeCKS transcripts in oncogene-transformed Rat-6 fibroblasts, and demonstrates that the transcription of SSeCKS was suppressed at least 15-fold in cells transformed by src and ras and roughly 3 to 4-fold in myc-transformed cells. Each lane of the gel used to generate the blot contained 30 micrograms of total RNA from Rat-6 cells transformed with the oncogenes indicated. The rat-6 lane contains total RNA from normal control cells. The levels of SSeCKS were also found to be down-regulated 10-fold in fos-transformed cells.

Figure 6:
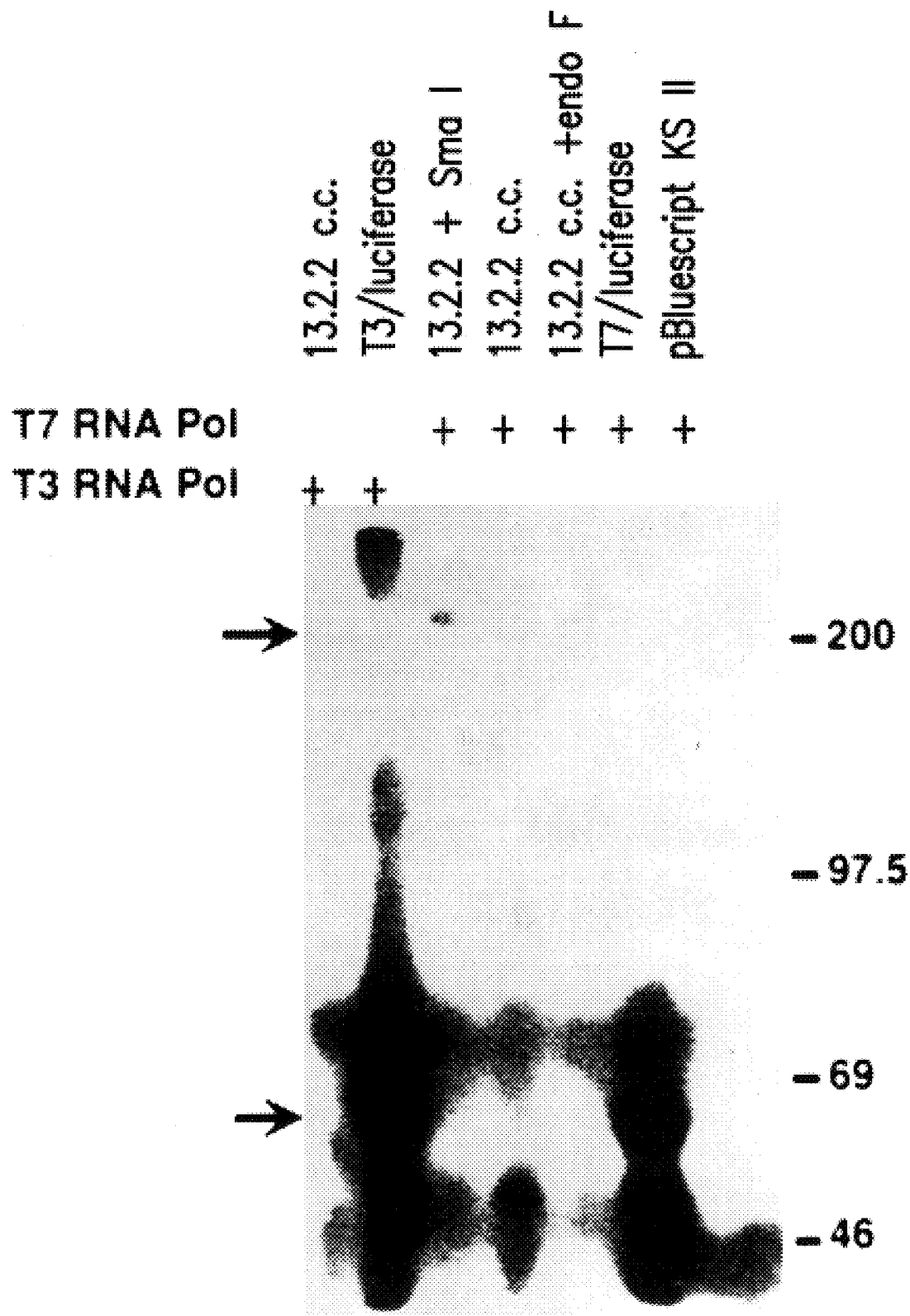
FIG. 6. Results of in vitro transcription-translation of SSeCKS cDNA.

FIG. 6 shows the results of in vitro transcription/translation of SSeCKS cDNA. The SSeCKS cDNA was cloned in a pBluescript II KS vector downstream of the T7 promoter, and analyzed by a coupled in vitro transcription/translation assay (TNT kit, Promega). In contrast to what was predicted, namely, a product with a molecular mass of 148.1 kDa, the 13.2.2 insert repeatedly yielded a 207 kDA product, as shown in the figure.

Figure 7A:
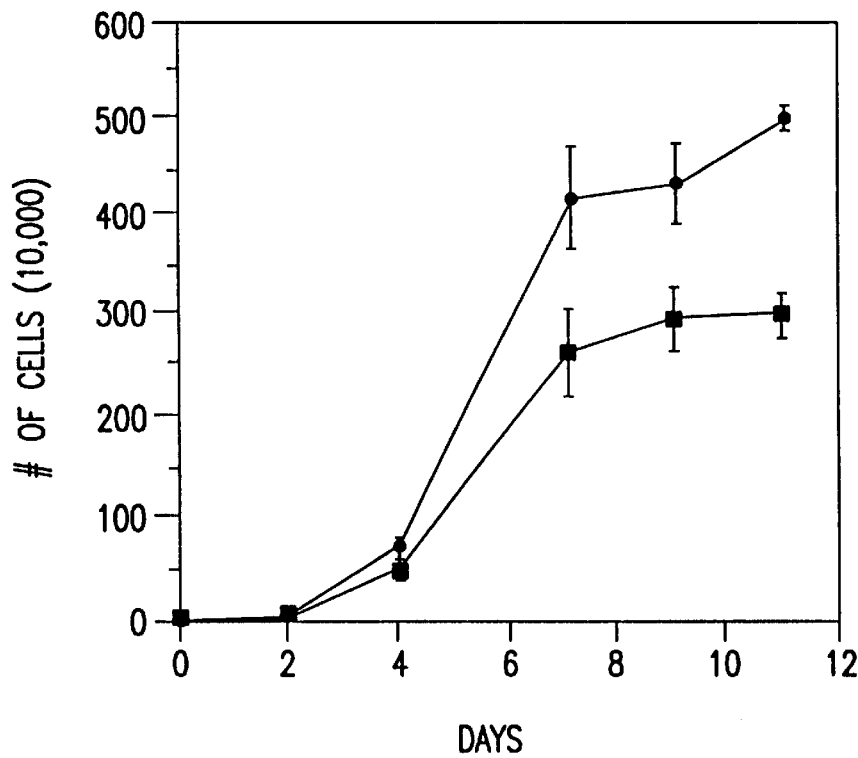
FIG. 7A & B. Proliferation of cells overexpressing SSeCKS.
Figure 7B:
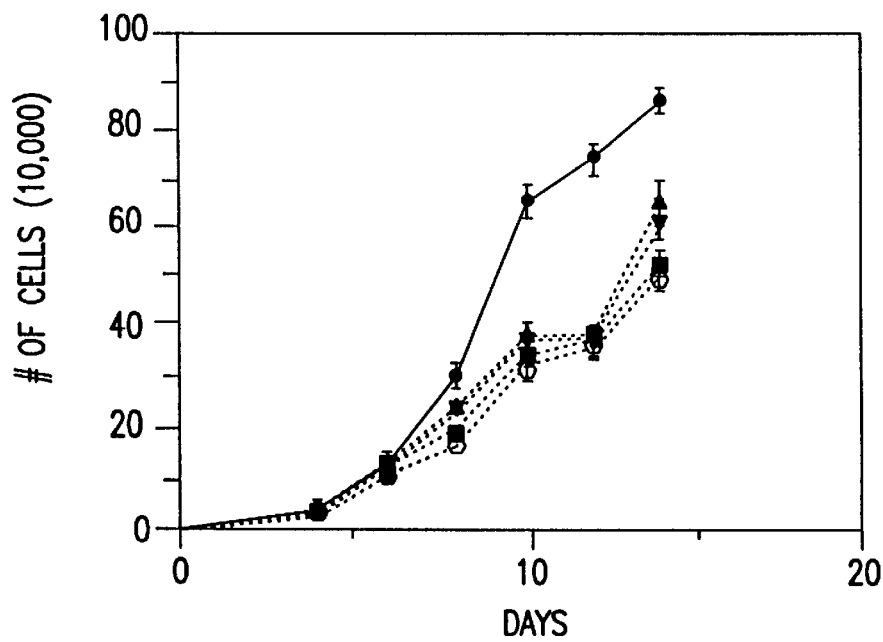

FIG. 7 shows the results of experiments which tested the effect of SSeCKS expression on the proliferation rates of untransformed omega packaging cells (NIH 3T3 background; panel A) or transformed cells (NIH/v-src; panel B) in the presence of serum growth factors. The SSeCKS cDNA (clone 13.2.2) was inserted into vector pBABFhygro, and transfected stably into the omega c packaging cells (panel A, solid circles). Vector alone was also transfected into these cells (open circles). Proliferation of the cells containing SSeCKS cDNA or vector alone was measured and compared (FIG. 7A). The cells were grown in media supplemented with 10% CS. FIG. 7A shows that after 4 weeks of passage, the growth rate of cells containing SSeCKS cDNA was 40% lower than that of cells containing vector alone.

Filtered supernatants from these packaging cell lines were used to infect NIH 3T3, Rat-6 and NIH/v-src—cells. Although the numbers of hygromycin resistant Rat-6 colonies arising from infection with the vector were similar to those arising from infection with SSeCKS, the initial growth rates of the colonies differed significantly. After 2 weeks, Rat-6/vector colonies were 3 to 5 mm in diameter whereas the Rat-6/SSeCKS colonies contained only 20–50 cells, indicating that SSeCKS is a negative regulator of mitogenesis.

Figure 8:
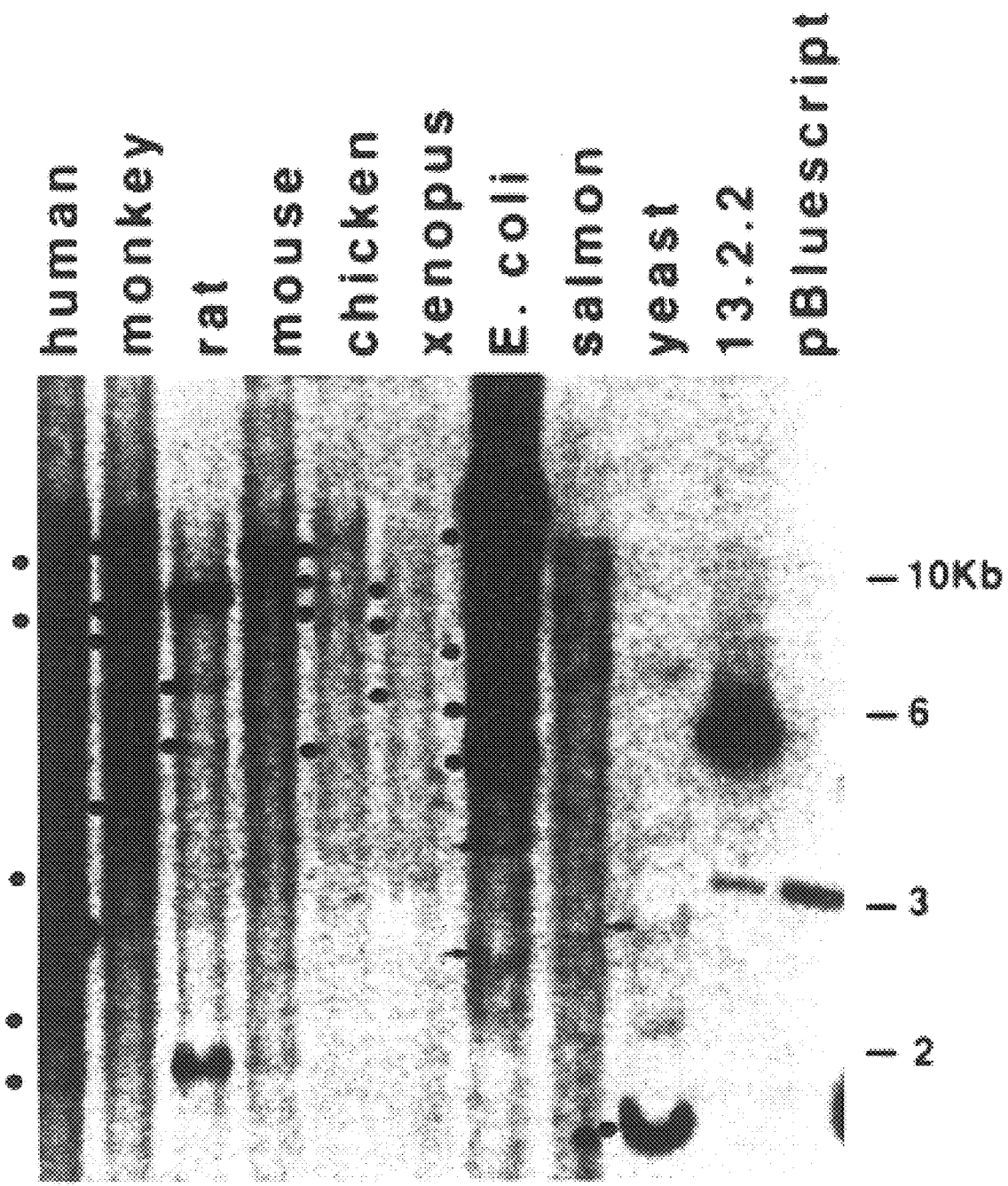
FIG. 8. "Zoo" Southern blot of SSeCKS probe to genomic DNA from various species.

FIG. 8 depicts the results of a Southern "Zoo" blot which measured hybridization of SSeCKS probe to DNA from a variety of species, namely genomic DNA from human (derived from HeLA cells), monkey (from CV-1 cells), rat (from Rat-6 cells), mouse (from NIH 3T3 cells), chicken (from chick embryo fibroblasts), Xenopus (from oocytes), *E. coli* (strain DH10), salmon sperm, and yeast cells. FIG. 8 confirms that rat and mouse 322 sequences are highly homologous. Furthermore, SSeCKS showed partial cross-hybridization to EcoRI bands from human, monkey, chicken, Xenopus, yeast, and *E. coli* DNA.

Figure 9:
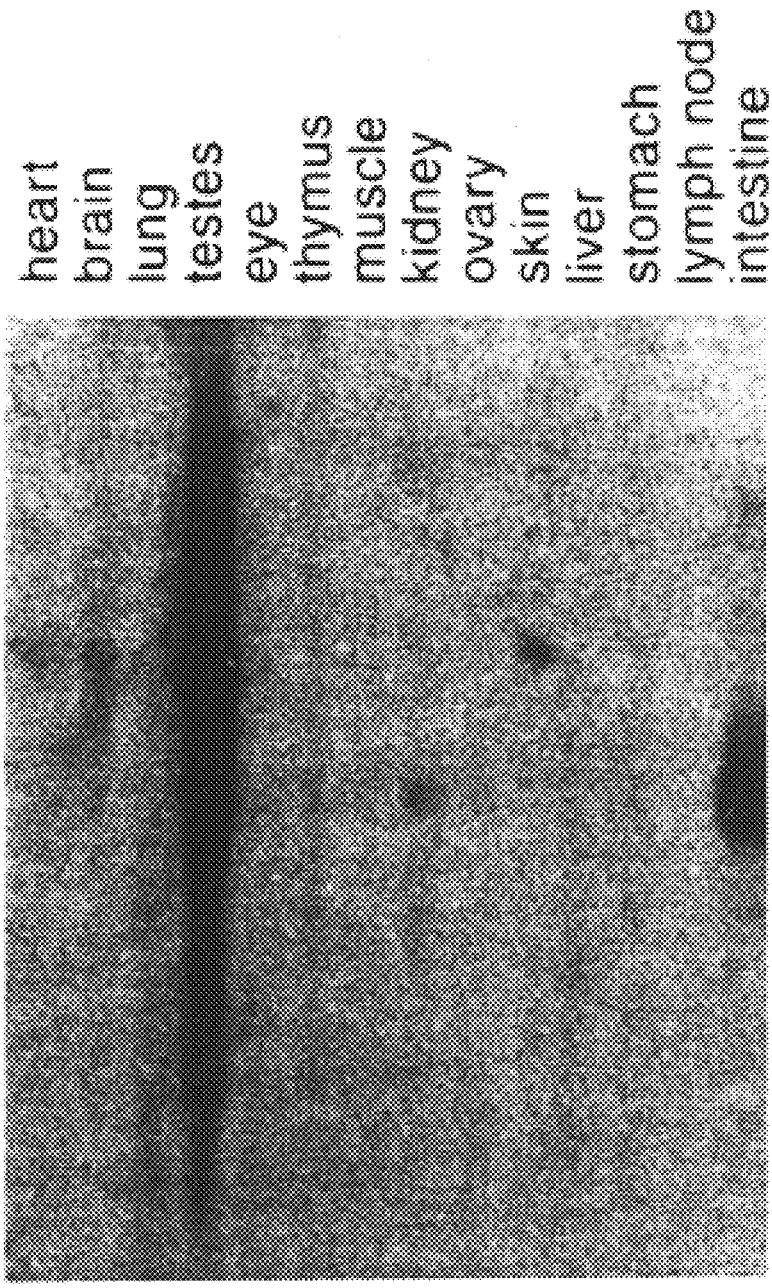
FIG. 9. Northern blot analysis showing tissue-specific expression of SSeCKS in mice.

FIG. 9 depicts the results of Northern blot analysis of SSeCKS expression in various mouse tissues. Approximately 5.4 kb transcripts were found to be abundantly expressed in testes, with 5–10 fold lower levels in skin, brain, and lung. A 3 kb transcript was also detected in intestines, with lower levels in kidney and stomach.

Figure 10:
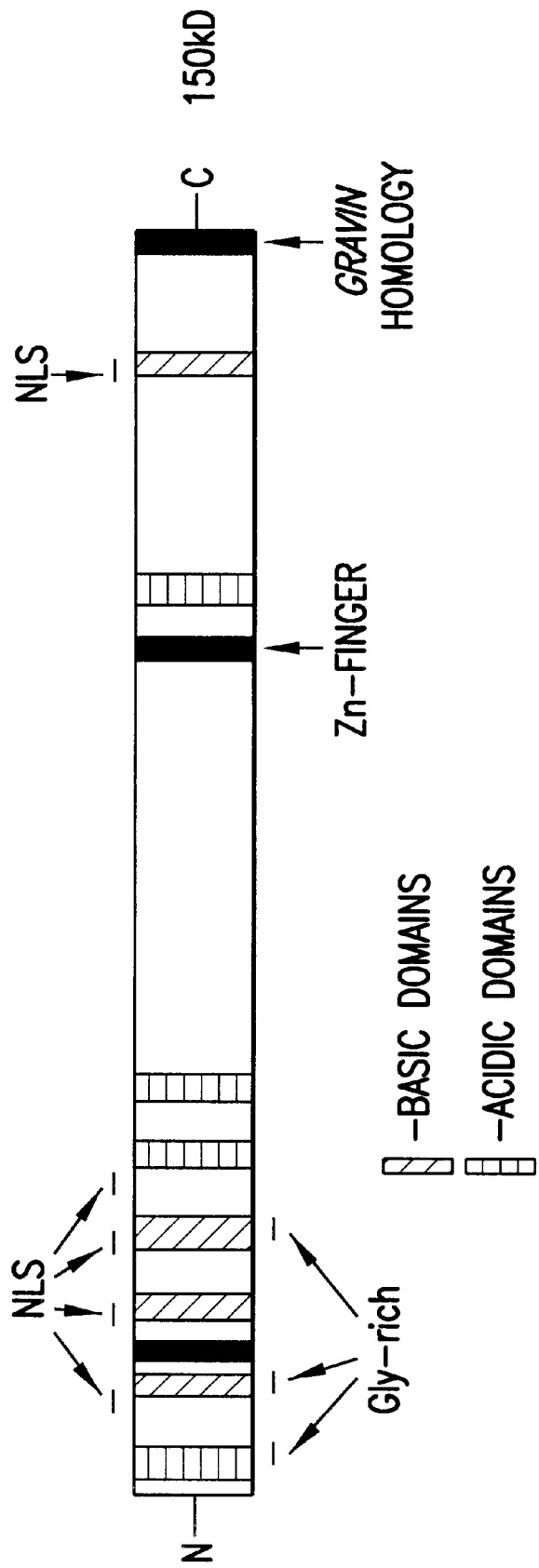
FIG. 10. Schematic diagram of SSeCKS protein.

FIG. 10 depicts a schematic diagram of the SSeCK protein, which contains several sequence motifs consistent with a role of transcriptional regulator, including a putative Zn finger, at least five nuclear localization signals, and several highly acidic domains typical of transactivation factors such as GAL4.

Various publications are cited herein, which are hereby incorporated by reference in their entireties.

What is claimed is:

1. An isolated nucleic acid molecule comprising the nucleic acid sequence set forth in SEQ ID NO.1.

2. A vector comprising the nucleic acid molecule of claim 1.

3. An isolated host cell comprising the nucleic acid molecule of claim 1.

* * * * *

UNITED STATES PATENT AND TRADEMARK OFFICE
CERTIFICATE OF CORRECTION

| | | |
|---|---|---|
| PATENT NO. | : 5,910,442 | Page 1 of 1 |
| APPLICATION NO. | : 08/635121 | |
| DATED | : June 8, 1999 | |
| INVENTOR(S) | : Irwin H. Gelman | |

It is certified that error appears in the above-identified patent and that said Letters Patent is hereby corrected as shown below:

Please replace the first paragraph at Col. 1 Line 4-7 with the following paragraph:

-- This invention was made with government support under NIH grant number CA 65787 awarded by the National Institutes of Health. The United States Government has certain rights in the invention. --

Signed and Sealed this

Twenty-second Day of September, 2009

David J. Kappos
*Director of the United States Patent and Trademark Office*

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 5134 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:1:

```
GGAAAAGACA GAGCCAGCCT CGGAGGAGCA GGAGCCGGCA GAAGACACAG ACCAGGCCAG      60
```

-continued

```
GTTGTCAGCA GACTACGAGA AGGTGGAGCT GCCTTTGGAA GACCAGGTTG GTGACCTGGA    120
GGCATCGTCA GAGGAGAAGT GTGCTCCTTT GGCAACGGAA GTGTTTGATG AGAAGATGGA    180
AGCCCACCAA GAAGTTGTTG CAGAGGTCCA CGTGAGCACC GTGGAGAAGA CAGAGGAGGA    240
GCAGGGAGGA GGAGGAGAGG CTGAAGGGGG CGTGGTGGTA AAGGAACAG GAGAATCCTT    300
GCCCCCTGAG AAACTGGCTG AGCCCCAGGA GGTCCCCCAG GAAGCTGAGC CTGCTGAGGA    360
GCTGATGAAG AGCAGAGAGA TGTGTGTCTC TGGAGGAGAC CACACTCAAC TGACAGACCT    420
AAGTCCTGAA GAGAAGACGC TGCCCAAACA CCCAGAAGGC ATTGTCAGTG AGGTGGAGAT    480
GCTGTCCTCT CAGGAAAGAA TCAAGGTACA GGGAAGTCCC TTGAAGAAAC TCTTCAGTAG    540
CTCAGGCTTA AAGAAGCTGT CTGGGAAGAA GCAGAAGGGG AAACGAGGAG GTGGGGGAGA    600
CGAAGAGCCT GGAGAATACC AACACATTCA CACCGAATCC CCAGAGAGTG CTGATGAGCA    660
GAAGGGAGAG AGCTCTGCGT CGTCCCCCGA GGAGCCTGAG GAGACCACGT GTCTGGAGAA    720
AGGGCCGCTG GAAGCACCCA GGATGGGGAA GCTGAGGAAG GAACTACTTC GTGGAGAGAA    780
GAAGAGGAAG GATCACTCCC TGGGCATCCT TCAAAAAGAT GGTGACACCC AAGAAACGGT    840
CCGAAGACCT TCTGAGAGTG ACAAGGAGGA AGAGCTGGAG AAGGTCAAGA GCGCCACCTT    900
GTCCTCCACT GATAGCACAG TGTCAGAAAT GCAAGATGAA GTCAAAACTG TTGGTGAGGA    960
ACAAAAGCCA GAGGAACCAA AGCGTAGGGT GGATACTTCA GTGTCTTGGG AAGCACTGAT   1020
TTGTGTCGGA TCATCCAAGA AGAGAGCAAG GAAGGCATCC TCTTCAGATA TAAGAGGGCC   1080
AAGGACACTG GGAGGGGGAC AGTCACAGAG CAGAGGAGGC CAGCAAAGAC AAAGAAGCCG   1140
AACAGACGCT GTTCCTGCCA GCACCCAGGA GCAGGACCAA GCGCAAGGAA GTTCCTCACC   1200
CGAGCCAGCG GGAAGCCCTT CCGAAGGGGA AGGTGTCTCC ACTTGGGAGT CATTTAAAAG   1260
ATTAGTCACT CCAAGAAAAA AATCCAAGTC AAAACTGGAA GAGAAAGAAG CCGGAAGGAC   1320
TCTAGTTGTA GGAGCAGGTT GTCCACTGAG ATCGAACCGT GTAGAGAAGA ATCTTGGGTT   1380
TCCATTAAGA AATTCATCCC CGGACGGCGG AAGAAAAGGG CAGATGGGAA GGCAAGAACA   1440
AGCCACTGTG GAAGACTCAG GGCCAGTGGA GATAAATGAG GACGAGCCTG ATGTCCCAGC   1500
CGTCGTGCCT CTGTCTGAGT ATGATGCAGT GGAGAGGGAG AAGATGGAAG CCCAGGGGAA   1560
TGCGGAGCTG CCCAGCTGCT GGGGCTGTGT AGTGTCCGAG GAGCTCAGTA AGACTCTGGT   1620
CCACACTGTG AGTGTCGCAG TCATTGATGG GACCAGGGCA GTCACCAGTG TCGAAGAGCG   1680
GTCTCCTTCG TGGATATCCG CTTCCGTAAC AGAACCTCTT GAACACACAG CGGGAGAAGC   1740
CATGCCACCT GTTGAAGAGG TCACTGAAAA AGACATCATT GCAGAAGAAA CTCCTGTGCT   1800
CACCCAGACG TTACCAGAGG GTAAAGATGC CCATGACGAC ATGGTCACCA GTGAAGTGGA   1860
TTTCACCTCA GAAGCTGTGA CAGCCACAGA GACCTCAGAG GCTCTCCGTA CTGAAGAAGT   1920
TACCGAAGCA TCGGGGGCCG AAGAGACCAC AGACATGGTG TCCGCAGTTT CCCAGCTGAC   1980
TGACTCCCCA GACACCACAG AGGAAGCCAC CCCAGTTCAG GAGGTAGAGG GTGGTGTGCT   2040
AGATACAGAA GAAGAGGAGC GCCAGACGCA GGCCATCCTC CAAGCCGTTG CAGACAAGGT   2100
GAAAGAGGAG TCCCAGGTGC CTGCAACCCA GACTGTGCAG AGAACGGGGT CAAAAGCACT   2160
GGAGAAGGTT GAGGAGGTAG AGGAGGACTC CGAAGTGCTG GCTTCGGAGA AAGAGAAGGA   2220
CGTTATGCCG AAAGGACCCG TGCAGGAAGC TGGAGCTGAG CATCTTGCAC AGGGCTCTGA   2280
GACTGGACAG GCTACTCCAG AGAGCCTTGA AGTTCCTGAA GTCACAGCAG ATGTAGACCA   2340
TGTCGCCACG TGCCAGGTTA TCAAGCTCCA GCAGCTGATG GAACAGGCCG TGGCCCCTGA   2400
GTCATCCGAA ACCTTGACAG ACAGTGAGAC AAATGGAAGC ACTCCCTTAG CAGATTCAGA   2460
```

```
CACTGCAGAT GGGACACAGC AAGATGAAAC CATTGACAGC CAGGACAGTA AAGCCACTGC    2520

AGCTGTCAGG CAGTCACAGG TCACAGAAGA GAGGCGGCT ACTGCTCAGA AAGAGGAGCC     2580

TTCGACACTA CCTAATAATG TTCCAGCCCA GGAAGAACAT GGGGAAGAAC CAGGAAGAGA    2640

TGTTCTTGAA CCTACACAGC AAGAGCTTGC TGCTGCAGCC GTGCCCGTCT GGCAAAAGAC    2700

TGAGGTGGGT CAAGAGGGTG AGGTTGACTG GTTGGATGGA GAAAAAGTCA AAGAAGAACA    2760

GGAGGTGTTT GTACACTCTG GACCCAACAG TCAAAAGGCT GCTGATGTGA CATATGACAG    2820

TGAAGTGATG GGAGTGGCCG GGTGTCAGGA AAAGGAGAGT ACTGAAGTGC AGAGTCTTAG    2880

CCTGGAGGAG GGAGAGATGG AAACTGACGT TGAAAAGGAG AAAAGGGAGA CAAAGCCAGA    2940

GCAAGTGAGT GAAGAAGGTG AGCAGGAAAC AGCCGCTCCT GAGCATGAAA GGAACTACGG    3000

GAAGCCAGTC CTGACACTTG ACATGCCCAG CTCAGAGAGG GGGAAGGCAC TGGGAAGCCT    3060

TGGAGGAAGC CCTTCTCTCC CAGACCAAGA CAAAGCAGGT TGCATAGAGG TTCAAGTTCA    3120

AAGCCTGGAC ACAACAGTCA CTCAAACAGC AGAAGCTGTG GAAAAGGTCA TAGAAACGGT    3180

TGTGATTTCA GAGACAGGTG AAAGTCCAGA GTGTGTAGGT GCACACTTAT TACCAGCTGA    3240

GAAGTCCTCT GCAACGGGTG GCCACTGGAC TCTTCAGCAT GCAGAGGACA CGGTACCCCT    3300

GGGGCCTGAG TCTCAGGCAG AATCCATCCC AATCATAGTA ACTCCTGCTC CTGAAAGCAC    3360

CCTACATCCT GACCTACAAG GAGAAATAAG CGCATCCCAG AGAGAGCGAT CAGAGGAAGA    3420

GGACAAGCCA GATGCTGGTC CTGATGCTGA CGGCAAGGAG AGTACAGCAA TCGACAAAGT    3480

CCTCAAGGCT GAACCTGAGA TCCTGGAACT TGAGAGTAAG AGCAACAAGA TTGTGCTGAA    3540

CGTCATTCAG ACAGCCGTTG ACCAGTTCGC ACGTACAGAA ACAGCCCCCG AAACTCATGC    3600

TTATGATTCA CAGACCCAGG TTCCTGCAAT GCGCTTGGAC AGCAGGGAGC CCAACAGATG    3660

CTGGACAAAA ATGAAAGTTG CCAAGATGAA ACACCCAGTG CCGCAGCCCA GAGAGGACTT    3720

GCAAGTCCTG ACCGTTCTGG AGGCATGGCT CAGCTCGGAA ATGCTTGCCG CGCTTGCAGT    3780

TGAAAGCGCC GGTGTCAAAG TAAGCATTGA GAAGCTGCCT CCTCAACCCA AAGATCAAAA    3840

GGAGCATGCT GCTGATGGCC CTCAGCTCCA AAGCTTAGCC CAGGCAGAGG CAGTGTCTGG    3900

AAACCTAACC AAAGAATCCC CAGACACCAA CGGACCAAAG CTAACCGAGG AGCGATGCCC    3960

CCAAAAGTTG AGGTCCAGGA AGAAGAAATG TCTACCAAGT CAGTCAAAGA GAACAAGGCC    4020

CAGGCAGAAG AGGACCTGCA GGAGCCAAAG GGAGACCTGG CAGAATCCTA AGATGTTAGT    4080

TGCTCATTGT ACATCTGTAA GACCAGAATG TGAAAACAAG TCACAGAACA AGATGCTGCT    4140

GTTGGGACCT TGGACCAAGA TTTCAGAGCC CATGAGATCC AGAGAGCAGG GCCGTCCAAT    4200

GATTTCCACC CAGTAGAGCA CCCCGACAAT TCTGAGGCTT CATCGGGAGC TAGAGCCAGC    4260

TAACATTTCC TCGTTTCAAG ACTGCCTTTG ATTTGCCCCT TGATGCCGTC CGTGTATTTC    4320

TAACATTTCC TCGTTTCAAG ACTGCCTTTG ATTTGCCCCT TGATGCCGTC CGTGTATTTC    4380

GGATTTAAGG TCCTGCGTTC TCAACCTGGA ACCAATTCTG CCATACCTAG TTCCACTTCT    4440

CAAACTGGAG CATCCTCCTT TATGTATTTA TATGTATGTT TTATGTAGTC CTCCTCCTGT    4500

ACCTATTGTA TATTTTTTC TAACGTTTAA GCACATGCTT TTTGTATTAT GCAATATATA     4560

ACGGGTGTGC AGCCATAGCG ACGCTTTGAA AAGCTCCAAG CCTCAACTGT AACCTGCAGC    4620

AAACAGATAA CATTCCTGGC AAGAAGAGAC AAGTCTTTTT TAAAGTTTAC TGATGCTTAG    4680

ATCTGTGGGC TTCTAGTCCT CTGAAAGTGG TTGTTTTCCT ATGCACAGCG AGCTCAGAAA    4740

TAAAAACCCC ATTTTGAAAC ATCCAGGATG TCCCAATATT ACCATGATTT TTTCCCCCCT    4800

TTTTGCTAAT CCAGTCCAGG TTGGAAAGAA GTCTCCTCTG TGTCAGATTA AGCCCTGTCT    4860
```

-continued

```
CTTAATGATA TGGACAAATG AGTGTGCCTA AGGCCATGAG ATGTTTCCTA ATGCAGAAGG    4920

AATCTGTTGT ACGTTTTTTT GATTGTACTC TTCTATGCTG GACCGAATTC ATATGCAGAT    4980

CGAAGTGAGT CCTGTTCTTT ACAGATGGTA TTTTGATAGA TACTGGAGTT TGTCTGTGTT    5040

ATATCTGTGC CCCTTCTTTA AGAACAATGT TGCATTATGT TCCTTTGGAT AAATTGTGAT    5100

TTGACAACTG ATTTAAATAA ACATATTTGA CTAC                                5134
```

(2) INFORMATION FOR SEQ ID NO:2:

(i) SEQUENCE CHARACTERISTICS:
        (A) LENGTH: 1346 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:2:

```
Met Glu Ala His Gln Glu Val Val Ala Glu Val His Val Ser Thr Val
 1               5                  10                  15

Glu Lys Thr Glu Glu Gln Gly Gly Gly Glu Ala Glu Gly Gly
            20                  25                  30

Val Val Val Glu Gly Thr Gly Glu Ser Leu Pro Pro Glu Lys Leu Ala
            35                  40                  45

Glu Pro Gln Glu Val Pro Gln Glu Ala Glu Pro Ala Glu Glu Leu Met
    50                  55                  60

Lys Ser Arg Glu Met Cys Val Ser Gly Gly Asp His Thr Gln Leu Thr
65                  70                  75                  80

Asp Leu Ser Pro Glu Glu Lys Thr Leu Pro Lys His Pro Glu Gly Ile
                85                  90                  95

Val Ser Glu Val Glu Met Leu Ser Ser Gln Glu Arg Ile Lys Val Gln
               100                 105                 110

Gly Ser Pro Leu Lys Lys Leu Phe Ser Ser Gly Leu Lys Lys Leu
           115                 120                 125

Ser Gly Lys Lys Gln Lys Gly Lys Arg Gly Gly Gly Asp Glu Glu
   130                 135                 140

Pro Gly Glu Tyr Gln His Ile His Thr Glu Ser Pro Glu Ser Ala Asp
145                 150                 155                 160

Glu Gln Lys Gly Glu Ser Ser Ala Ser Ser Pro Glu Glu Pro Glu Glu
                165                 170                 175

Thr Thr Cys Leu Glu Lys Gly Pro Leu Glu Ala Pro Arg Met Gly Lys
            180                 185                 190

Leu Arg Lys Glu Leu Leu Arg Gly Glu Lys Arg Lys Asp His Ser
        195                 200                 205

Leu Gly Ile Leu Gln Lys Asp Gly Asp Thr Gln Glu Thr Val Arg Arg
    210                 215                 220

Pro Ser Glu Ser Asp Lys Glu Glu Leu Glu Lys Val Lys Ser Ala
225                 230                 235                 240

Thr Leu Ser Ser Thr Asp Ser Thr Val Ser Glu Met Gln Asp Glu Val
                245                 250                 255

Lys Thr Val Gly Glu Glu Gln Lys Pro Glu Glu Pro Lys Arg Arg Val
```

-continued

```
                     260                      265                      270
Asp Thr Ser Val Ser Trp Glu Ala Leu Ile Cys Val Gly Ser Ser Lys
        275                      280                      285
Lys Arg Ala Arg Lys Ala Ser Ser Ser Asp Ile Arg Gly Pro Arg Thr
290                      295                      300
Leu Gly Gly Gly Gln Ser Gln Ser Arg Gly Gly Gln Gln Arg Gln Arg
305                      310                      315                      320
Ser Arg Thr Asp Ala Val Pro Ala Ser Thr Gln Glu Gln Asp Gln Ala
                     325                      330                      335
Gln Gly Ser Ser Ser Pro Glu Pro Ala Gly Ser Pro Ser Glu Gly Glu
                     340                      345                      350
Gly Val Ser Thr Trp Glu Ser Phe Lys Arg Leu Val Thr Pro Arg Lys
        355                      360                      365
Lys Ser Lys Ser Lys Leu Glu Glu Lys Glu Ala Gly Arg Thr Leu Val
        370                      375                      380
Val Gly Ala Gly Cys Pro Leu Arg Ser Asn Arg Val Glu Lys Asn Leu
385                      390                      395                      400
Gly Phe Pro Leu Arg Asn Ser Ser Pro Asp Gly Gly Arg Lys Gly Gln
                     405                      410                      415
Met Gly Arg Gln Glu Gln Ala Thr Val Glu Asp Ser Gly Pro Val Glu
                     420                      425                      430
Ile Asn Glu Asp Glu Pro Asp Val Pro Ala Val Val Pro Leu Ser Glu
        435                      440                      445
Tyr Asp Ala Val Glu Arg Glu Lys Met Glu Ala Gln Gly Asn Ala Glu
        450                      455                      460
Leu Pro Ser Cys Trp Gly Cys Val Val Ser Glu Glu Leu Ser Lys Thr
465                      470                      475                      480
Leu Val His Thr Val Ser Val Ala Val Ile Asp Gly Thr Arg Ala Val
                     485                      490                      495
Thr Ser Val Glu Glu Arg Ser Pro Ser Trp Ile Ser Ala Ser Val Thr
                     500                      505                      510
Glu Pro Leu Glu His Thr Ala Gly Glu Ala Met Pro Pro Val Glu Glu
        515                      520                      525
Val Thr Glu Lys Asp Ile Ile Ala Glu Glu Thr Pro Val Leu Thr Gln
        530                      535                      540
Thr Leu Pro Glu Gly Lys Asp Ala His Asp Asp Met Val Thr Ser Glu
545                      550                      555                      560
Val Asp Phe Thr Ser Glu Ala Val Thr Ala Thr Glu Thr Ser Glu Ala
                     565                      570                      575
Leu Arg Thr Glu Glu Val Thr Glu Ala Ser Gly Ala Glu Glu Thr Thr
                     580                      585                      590
Asp Met Val Ser Ala Val Ser Gln Leu Thr Asp Ser Pro Asp Thr Thr
        595                      600                      605
Glu Glu Ala Thr Pro Val Gln Glu Val Glu Gly Val Gly Val Leu Asp Thr
        610                      615                      620
Glu Glu Glu Glu Arg Gln Thr Gln Ala Ile Leu Gln Ala Val Ala Asp
625                      630                      635                      640
Lys Val Lys Glu Glu Ser Gln Val Pro Ala Thr Gln Thr Val Gln Arg
                     645                      650                      655
Thr Gly Ser Lys Ala Leu Glu Lys Val Glu Glu Val Glu Glu Asp Ser
                     660                      665                      670
Glu Val Leu Ala Ser Glu Lys Glu Lys Asp Val Met Pro Lys Gly Pro
        675                      680                      685
```

-continued

```
Val Gln Glu Ala Gly Ala Glu His Leu Ala Gln Gly Ser Glu Thr Gly
        690                 695                 700
Gln Ala Thr Pro Glu Ser Leu Glu Val Pro Glu Val Thr Ala Asp Val
705                 710                 715                 720
Asp His Val Ala Thr Cys Gln Val Ile Lys Leu Gln Gln Leu Met Glu
                725                 730                 735
Gln Ala Val Ala Pro Glu Ser Ser Glu Thr Leu Thr Asp Ser Glu Thr
        740                 745                 750
Asn Gly Ser Thr Pro Leu Ala Asp Ser Asp Thr Ala Asp Gly Thr Gln
        755                 760                 765
Gln Asp Glu Thr Ile Asp Ser Gln Asp Ser Lys Ala Thr Ala Ala Val
        770                 775                 780
Arg Gln Ser Gln Val Thr Glu Glu Ala Ala Thr Ala Gln Lys Glu
785                 790                 795                 800
Glu Pro Ser Thr Leu Pro Asn Asn Val Pro Ala Gln Glu Glu His Gly
                805                 810                 815
Glu Glu Pro Gly Arg Asp Val Leu Glu Pro Thr Gln Gln Glu Leu Ala
        820                 825                 830
Ala Ala Ala Val Pro Val Trp Gln Lys Thr Glu Val Gly Gln Glu Gly
        835                 840                 845
Glu Val Asp Trp Leu Asp Gly Glu Lys Val Lys Glu Gln Glu Val
850                 855                 860
Phe Val His Ser Gly Pro Asn Ser Gln Lys Ala Ala Asp Val Thr Tyr
865                 870                 875                 880
Asp Ser Glu Val Met Gly Val Ala Gly Cys Gln Glu Lys Glu Ser Thr
                885                 890                 895
Glu Val Gln Ser Leu Ser Leu Glu Gly Glu Met Glu Thr Asp Val
        900                 905                 910
Glu Lys Glu Lys Arg Glu Thr Lys Pro Glu Gln Val Ser Glu Glu Gly
        915                 920                 925
Glu Gln Glu Thr Ala Ala Pro Glu His Glu Arg Asn Tyr Gly Lys Pro
        930                 935                 940
Val Leu Thr Leu Asp Met Pro Ser Ser Glu Arg Gly Lys Ala Leu Gly
945                 950                 955                 960
Ser Leu Gly Gly Ser Pro Ser Leu Pro Asp Gln Asp Lys Ala Gly Cys
                965                 970                 975
Ile Glu Val Gln Val Gln Ser Leu Asp Thr Thr Val Thr Gln Thr Ala
                980                 985                 990
Glu Ala Val Glu Lys Val Ile Glu Thr Val Ile Ser Glu Thr Gly
        995                 1000                1005
Glu Ser Pro Glu Cys Val Gly Ala His Leu Leu Pro Ala Glu Lys Ser
        1010                1015                1020
Ser Ala Thr Gly Gly His Trp Thr Leu Gln His Ala Glu Asp Thr Val
025                 1030                1035                1040
Pro Leu Gly Pro Glu Ser Gln Ala Glu Ser Ile Pro Ile Val Thr
                1045                1050                1055
Pro Ala Pro Glu Ser Thr Leu His Pro Asp Leu Gln Gly Glu Ile Ser
                1060                1065                1070
Ala Ser Gln Arg Glu Arg Ser Glu Glu Glu Asp Lys Pro Asp Ala Gly
        1075                1080                1085
Pro Asp Ala Asp Gly Lys Glu Ser Thr Ala Ile Asp Lys Val Leu Lys
                1090                1095                1100
Ala Glu Pro Glu Ile Leu Glu Leu Glu Ser Lys Ser Asn Lys Ile Val
105                 1110                1115                1120
```

-continued

```
Leu Asn Val Ile Gln Thr Ala Val Asp Gln Phe Ala Arg Thr Glu Thr
            1125                1130                1135

Ala Pro Glu Thr His Ala Tyr Asp Ser Gln Thr Gln Val Pro Ala Met
            1140                1145                1150

Arg Leu Asp Ser Arg Glu Pro Asn Arg Cys Trp Thr Lys Met Lys Val
            1155                1160                1165

Ala Lys Met Lys His Pro Val Pro Gln Pro Arg Glu Asp Leu Gln Val
        1170                1175                1180

Leu Thr Val Leu Glu Ala Trp Leu Ser Ser Glu Met Leu Ala Ala Leu
185                 1190                1195                1200

Ala Val Glu Ser Ala Gly Val Lys Val Ser Ile Glu Lys Leu Pro Pro
            1205                1210                1215

Gln Pro Lys Asp Gln Lys Glu His Ala Ala Asp Gly Pro Gln Leu Gln
            1220                1225                1230

Ser Leu Ala Gln Ala Glu Ala Val Ser Gly Asn Leu Thr Lys Glu Ser
            1235                1240                1245

Pro Asp Thr Asn Gly Pro Lys Leu Thr Glu Glu Arg Cys Pro Gln Lys
        1250                1255                1260

Leu Arg Ser Arg Lys Lys Lys Cys Leu Pro Ser Gln Ser Lys Arg Thr
265                 1270                1275                1280

Arg Pro Arg Gln Lys Arg Thr Cys Arg Ser Gln Arg Glu Thr Trp Gln
            1285                1290                1295

Asn Pro Lys Met Leu Val Ala His Cys Thr Ser Val Arg Pro Glu Cys
            1300                1305                1310

Glu Asn Lys Ser Gln Asn Lys Met Leu Leu Leu Gly Pro Trp Thr Lys
        1315                1320                1325

Ile Ser Glu Pro Met Arg Ser Arg Glu Gln Gly Arg Pro Met Ile Ser
    1330                1335                1340

Thr Gln
1345
```